US007104950B2

(12) United States Patent
Levy

(10) Patent No.: US 7,104,950 B2
(45) Date of Patent: Sep. 12, 2006

(54) SEXUAL STIMULATION

(75) Inventor: David H. Levy, Cambridge, MA (US)

(73) Assignee: Th, Inc., Cambridge, MA (US)

( * ) Notice: Subject to any disclaimer, the term of this patent is extended or adjusted under 35 U.S.C. 154(b) by 187 days.

(21) Appl. No.: 10/260,330

(22) Filed: Sep. 30, 2002

(65) Prior Publication Data

US 2003/0073881 A1 Apr. 17, 2003

Related U.S. Application Data

(63) Continuation-in-part of application No. 09/609,526, filed on Jul. 3, 2000, now abandoned.

(60) Provisional application No. 60/141,884, filed on Jul. 2, 1999.

(51) Int. Cl.
*A61F 5/00* (2006.01)

(52) U.S. Cl. .......................................................... 600/38

(58) Field of Classification Search ........ 446/220–226; 600/29–32, 38–41; 606/198, 197, 192, 193; 601/76, 77, 96

See application file for complete search history.

(56) References Cited

U.S. PATENT DOCUMENTS

| | | | | | |
|---|---|---|---|---|---|
| 494,410 | A | * | 3/1893 | Carpenter | 446/183 |
| 734,498 | A | * | 7/1903 | Bachler | 606/192 |
| 1,413,789 | A | * | 4/1922 | Schaff | 606/192 |
| 1,729,296 | A | * | 9/1929 | Sarason | 607/105 |
| 3,259,132 | A | * | 7/1966 | Katter | 30/324 |
| 3,495,589 | A | | 2/1970 | Clement | |
| 3,598,106 | A | | 8/1971 | Buning | |
| 3,752,150 | A | | 8/1973 | Harris | |
| 3,991,751 | A | | 11/1976 | O'Rourke | |
| 3,996,930 | A | | 12/1976 | Sekulich | |
| 4,050,449 | A | | 9/1977 | Castellana et al. | |
| 4,167,938 | A | | 9/1979 | Remih | |
| 4,776,347 | A | | 10/1988 | Matthews | |
| 5,072,720 | A | * | 12/1991 | Francis et al. | 600/186 |
| 5,131,906 | A | * | 7/1992 | Chen | 600/29 |
| 5,256,123 | A | | 10/1993 | Reinbolt | |
| 5,573,499 | A | | 11/1996 | McAllister | |
| 5,674,238 | A | | 10/1997 | Sample et al. | |
| 5,690,603 | A | | 11/1997 | Kain | |
| 5,690,605 | A | | 11/1997 | Hamlin et al. | |
| 5,704,894 | A | | 1/1998 | Boutos | |
| 5,724,994 | A | | 3/1998 | Simon et al. | |
| 5,885,205 | A | | 3/1999 | Kassman | |
| 6,165,108 | A | | 12/2000 | Ralston | |
| 6,179,795 | B1 | | 1/2001 | Garza | |

* cited by examiner

*Primary Examiner*—Samuel G. Gilbert
(74) *Attorney, Agent, or Firm*—Fish & Richardson P.C.

(57) ABSTRACT

A predominantly solid, phallus-shaped, semi-rigid device with an internal mechanism that expands designated surface regions outwardly to change the shape of the device. A fluid filled reservoir located at one end of the device expresses fluid through internal channels, causing the resilient expansion at specified surface regions due to a locally reduced cross section. A sexual preference transfer function that combines the masturbatory action of a first person with the expressed or non-expressed sexual preferences of a second person. A sexual preference transfer function is utilized to improve the control or influence of a sexual pleasure device in contact with a second person based on autonomic and/or manually collected data.

67 Claims, 10 Drawing Sheets

FIG. 31

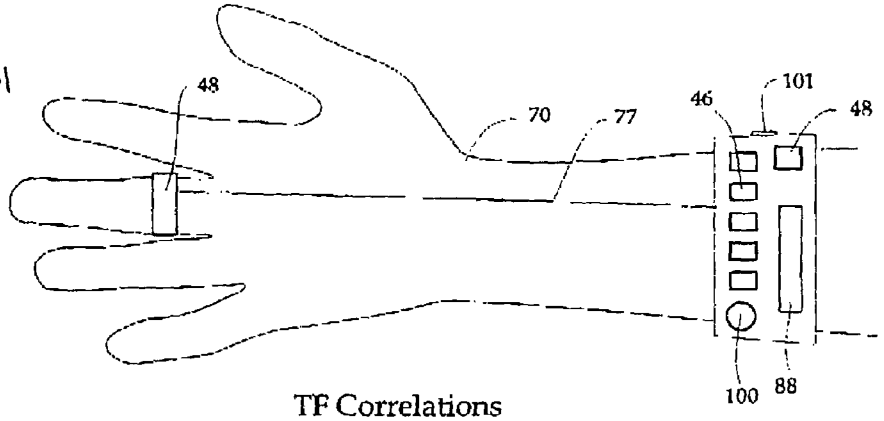

FIG. 32

TF Correlations

| Source | Input data | | Output response |
|---|---|---|---|
| First person | hand amplitude | | |
| | hand Frequency | | |
| | hand Force | | |
| | hand Direction<br>Auxillary hand motion | | |
| | Voice | | Amplitude |
| Second person | Amplitude | | Frequency |
| | Frequency | | Force |
| | Force | | Direction |
| | Direction | Transfer Function | Auxillary motion |
| | Auxillary motion | | |
| | Physiologic data | | |
| | Voice | | |
| Climax button | On/off | | |
| Intensity dial | Magnitude | | |
| Stored Control Data | | | |

Note: All inputs can be duration and time dependent.

SEXUAL STIMULATION

CROSS-REFERENCE TO RELATED APPLICATIONS

This application is a continuation-in-part (and claims the benefit of priority under 35 USC 120) of U.S. application Ser. No. 09/609,526, filed Jul. 3, 2000 now abandoned, and also claims priority under 35 USC 119(e) of provisional application No. 60/141,884, filed Jul. 2, 1999. The disclosure of the prior applications is considered part of (and is incorporated by reference in) the disclosure of this application.

TECHNICAL FIELD

This invention relates to devices and methods used for sexual pleasure, and specifically to an artificial phallus and a method of its use.

BACKGROUND

There is a growing acceptance of sexuality, as exhibited by popular acceptance of the near-universality of masturbation, the growth of the market for sexual devices, and the open discussion of topics such as "cyber sex" (internet discussion) and "phone sex." Prior to this shift there have been a plethora of devices sold for sexual pleasure, although primarily under euphemistic names and a pretense of providing "massage." The history extends at least as far as ancient Greece, where such devices were called "olisbos." Modern devices fall broadly into two classes: mechanized and non-mechanized. Mechanized devices typically vibrate, although there are examples that rotate, thrust, and even circulate small beads within an elastomeric shell. Non-mechanized devices are made from a solid mass of rigid or semi-rigid material in a variety of shapes. One example is provided by U.S. Pat. No. 5,690,603 to Kain, a device that may be "worn" by a partner without the need of straps or belts. The device includes a hollow core that contains a fluid, allowing the partners to force fluid back and forth by muscular activity through an area of reduced diameter, thereby creating an increase of the velocity of the fluid and increased stimulation in the accepting partner.

U.S. Pat. No. 3,752,150 to Harris discloses an exercise device wherein the strength of the vaginal musculature is determined by measuring the pressure of a liquid in a pliable hollow elongated member with a manometer. The device is pressurized by a syringe through a tube. To operate the device, the core member is isolated from the syringe by a first valve and opened to the manometer by a second valve. Muscular contraction then forces fluid into the manometer to provide a measure of vaginal strength.

What would be desirable is a single device that varies in size during use. It would also be desirable for a single device to vary in form (i.e. shape) during use. It would be yet further desirable for this variation to be integral to the traditional operation of the device. It would be yet further desirable to provide variable sized and shaped features in an asymmetric fashion so that the user may have a further level of sensation control. It would further be desirable to provide surface features (such as bumps, undulations, knobs, and ridges) that would appear and disappear during use. It would further be desirable to provide radial increase along selected portions of the length of the shaft to accommodate specific predilections. It would be desirable to have a finger-like protrusion at the tip of a device that extends and retracts while inside the body, providing an internal "tickling" effect. It would further be desirable to omit radial increase (i.e. provide a constant and unchanging radius) along selected portions of the length of the shaft to accommodate specific predilections. It would be further desirable to provide these features with structural integrity to provide sufficient rigidity between the tip and the base of the device so that lateral and torque forces may be transmitted from one end to the other. And, it would be desirable for these dynamic variations to be controllable simultaneously and interchangeably while being transparent to the normal use of the device, including the ability to insert, withdraw, rotate, and actuate the variable radius (and shape) features with one hand, without readjusting or re-orienting the hand. This is important as it frees the other hand. It would be yet further desirable to provide two independently controllable ranges of shape changes within the same device, so that in one hand orientation a first range of overall shapes is available by squeezing and releasing an end of the device, and in a second hand orientation a second range of overall shape may be so attained. It would also be desirable for an artificial phallus to be used by a person on themselves while there hands were located near their chest.

While cyber and phone sex are becoming more accepted, no device or system is available that provides a physical affect on a remotely located partner, although the concept has been raised. Sexual relations at a distance have been characterized as including haptic gloves that provide the tactile sensation of a person at a distance, a purely mental connection or remotely controlled sexual devices that allow one partner to satisfy another. In each case the concept is either beyond the range of technologic possibility or provides a system in which one party gives sexual pleasure and one receives.

What is desirable is a system that provides sexual sharing that can be transparent to both parties (i.e. one party should not be focused on the control of a device for the other partner). It is desirable to provide a system that allows the motions of self-pleasure of a first person to influence the sensations provided to a second person in a way that is transparent to the first person. It is further desirable to provide this functionality in a simultaneous reciprocal manner. It is further desirable to provide a system that allows sexual partners with differing sexual patterns to each have their disparate needs addressed simultaneously.

SUMMARY

The limitations described above are superceded, and objects and advantages achieved by a phallus-shaped device (a dildo) with a selectively variable radius. The object is to provide a means to selectively change the size and shape of regions of the shaft of the device. Note that changing shape is different than merely changing size, as the latter is merely "growing" uniformly i.e. changing scale. In one embodiment the variability is provided by a fluid means, such as air, water, or oil. A nearly-solid elastomeric dildo includes internal molded-in channels, either along the surface, or leading to internal volumes close to the surface. These channels are open to a primary reservoir rigidly secured at the end of the device that remains outside the body. The channels and reservoir are fluid filled. By squeezing the reservoir end, the user forces the fluid into the channels, causing them to increase in size, thereby increasing the radius of the device in at least one region. This action stores energy in the material that constitutes the expandable webbing, energy which is released as the material forces the fluid back into the primary reservoir. The primary reservoir is preferably larger than the diameter of the device, thereby providing sufficient radial expansion of the device during use. The degree of expansion of each channel or sub-regions within each channel is controlled by the molded thickness of material on the exterior side of each region of the channel and the type of material selected. The location of the primary reservoir at the end of and integral with the device allows the user to perform a plurality of actions with one hand, namely motion of the device (insertion and removal) actuation of a first range of motion of the device (inflation and deflation) as well as rotation of the device, the latter being significant as some of the embodiments include asymmetric features. All of these motions may be affected in any order, at any time, and with one hand, thereby freeing the other hand to perform additional tasks. Reorientation of the hand is not necessary to control a first range of motion, although in one embodiment (with two independent sets of surface features) a second range or type of motions is available by reorientation of the hand.

Variations in radius or shape can occur in selected locations by modifying the interior shape and location of the channels, specifically, by varying the thickness of the wall between the exterior surface of the device and the channel that contains the fluid. Channels may be shaped so that ridges appear and disappear as the reservoir is squeezed. Regions designed with thicker sections between the channel and the surface of the device will expand less while thin sections will expand more, providing a variety of embodiments including devices with regular undulations, randomized undulations, textures, and knobs. There are also embodiments in which there is no expansion at all in selected localized regions along the length of the shaft, such as at the tip, base or center, thereby providing specialized devices for various anatomies and preferences. For example, a region of increasing diameter may be concentrated at the end of the device opposite the reservoir, forming a bulbous head. One embodiment includes inwardly molded features that invert momentarily to provide outward projections. In one embodiment, closely mimicking the human anatomy, the expansion is localized to two opposing sides along the length of the shaft, separated by regions of non-expansion. There are also embodiments in which the device's expansion is localized on one side of the shaft, providing a strong lateral asymmetry, so that by rotating the device the user may experience distinctly different sensations as portions of the anatomy are selectively stimulated or ignored. The device provides sufficient rigidity between the tip of the device and the base of the device so that it acts as a unitary member. This allows the user to selectively apply forces at the distal tip when inserted within the body (especially forces with a lateral component, i.e. perpendicular to the primary axis of the device) an important aspect of such a device. Another way to express this is that the connection between the reservoir and the proximal end of the shaft should be attached with sufficiently rigidity that a useful amount of torque may be transmitted from the hand grasping the reservoir to the proximal end of the shaft. In turn, the shaft itself should be sufficiently rigid that a torque placed upon the proximal end of the shaft should transmit through the shaft to the distal end, rather than cause lateral or internal buckling. One embodiment includes two shape changing features that may be independently actuated, utilizing one or two reservoirs. In one use mode, squeezing and releasing with the hand held in a first orientation, provides a first overall range of shapes from the device, while holding the device in a second orientation, provides a second overall range of shapes. One may also control both ranges merely by squeezing the hand in different ways, such as only at the finger tips, or also squeezing at the palm.

One embodiment uses a two-piece design in which the distal end is comprised of thin webbing over an internal core. A primary advantage of this construction is that it provides a solid (rather than fluid) support behind the webbing when the device is in its relaxed state. The result is a near-constant feel between the expansive and non-expansive regions of the device. An interference fit between at the neck region that supports this internal core provides a rigid attachment. Narrow ducts, preferably molded in the core, allow fluid to pass through the area of interference fit to reach the expansive area at the tip. Because the core is passed through a relatively narrow passage, it is useful to assemble the device with the aid of a vacuum fixture to expand the device outwardly. (Note: pressurized air is also useful to blow mold, or to remove some embodiments from the tooling as they may involve complex geometries and/or undercuts.) One material that produces good parts is a tin-based silicone, durometer 30 on the shore A scale. In one embodiment, the device is manufactured by containing the fluid in a custom-shaped balloon, prior to molding. The balloon is held to a central core by a low-tack adhesive. This facilitates manufacturing the devices in a single step. In other embodiments the balloon functionality is provided by a temporary rigid structure that degrades into the fluid over a relatively short period of time. Another embodiment utilizes a screw-shaped core to provide intermittent ridges oriented predominantly perpendicular to the shaft axis, yet in a shape that can be easily removed.

In another embodiment the size variation is provided mechanically. The size variation may also be actuated remotely, by a second person (either actively or passively, as described in detail below) through phone lines or the Internet by utilizing the signal to drive a pump or motor. Obviously, the device can be made to vibrate. A clear elastomeric material and a colored and/or particulate filled fluid may be used to provide a novel appearance. In another embodiment the device may be designed to fit in a harness so that it may be worn, and rather than actuated by hand, expansion occurs when the bodies press together, compacting the reservoir between them. Also, the dynamic dildo designs disclosed may be made with two shafts.

In another embodiment, an extension protrudes from the base of a dildo at approximately a right angle, providing an easier means for a person using the dildo on themselves to hold it. In another embodiment a finger-like elastomeric protrusion is disposed along this extension and oriented to point in the same direction as the dildo itself. In one embodiment the attachment point of the protrusion may be selected by the user. In another embodiment the exposed end of the extension has a handle that extends from the end of the extension above, in the same direction as the dildo. This allows a person using the device on themselves to grasp a dildo with their hands in a natural position near their chest or stomach. The protrusion may also be molded into the handle to form a surface as much as several inches wide so that the material contacting the exterior portion of the body is surface-like, rather than finger-like.

The two devices disclosed above may be incorporated into a single device in which the variable expansion occurs when the handle is squeezed.

Another aspect of the invention features a method of providing sexual pleasure. The method includes grasping a phallus-shaped device with a first hand, moving the device in a predominantly linear reciprocal motion, and, while grasping said device with said first hand, radially expanding a first portion of a shaft of said device with said first hand.

In some embodiments, radially expanding the first portion of the shaft changes an overall shape of the shaft. In some cases, the method also includes returning the shaft to an original state by relaxing the grasp of the first hand.

In some instances, the change of shape is effected through fluid displacement.

Preferably, the shaft includes a second portion that maintains essentially a constant radius as the first portion is radially expanded. For example, the shaft may have a wall thickness in its second portion greater than a wall thickness in its first portion.

In some embodiments, the second portion of the shaft is radially solid. The first and second portions may extend side-by-side along the shaft, or the second portion may form a band about a circumference of the shaft, as examples.

In some situations, radially expanding the first portion of the shaft includes increasing a size of a localized feature at an outer surface of the shaft.

In some cases, the moving of the device and the radial expansion occur simultaneously.

Sometimes the moving of the device and the radial expansion are performed while holding the device with the first hand in a single grip orientation.

In some embodiments, the first hand grasps a deformable portion of the phallus-shaped device containing a fluid reservoir. The deformable portion may have a significantly larger diameter than the shaft, for example.

The method may also includes transmitting a lateral force as applied by the hand grasping the reservoir to a distal end of the device through a relatively rigid connection therebetween.

According to another aspect of the invention, a device for sexual pleasure includes a longitudinally rigid shaft portion for insertion into a human body, the shaft portion having a radially-expandable exterior surface in a discrete region thereof, and a graspable portion rigidly secured to one end of the shaft portion and containing a manually manipulable fluid reservoir in hydraulic communication with the radially-expandable surface for altering an outer shape of the shaft portion in response to manual manipulation of the graspable portion.

Preferably, the graspable portion is attached to the shaft for transmitting a manually-induced motion from the graspable portion to the shaft portion.

The graspable portion is of a greater diameter than the shaft portion in some preferred constructions.

In some embodiments, the radially-expandable surface is asymmetrically oriented on the shaft portion.

The shaft portion also includes a non-deformable surface region in some embodiments. The non-deformable surface region may be disposed in an orientation from a list consisting of: linearly along a length of the shaft, near a distal end of the shaft, near a proximal end of the shaft, intermittently along a length of the shaft, and asymmetrically disposed upon one side of the shaft.

In some configurations, the radially-expandable surface is an exposed surface of an outer wall of the shaft portion that varies in thickness along the radially-expandable surface.

In some instances, the radially-expandable surface has a contoured exterior surface when radially expanded. The contoured exterior surface may define undulations, for example.

Preferably, the graspable portion is attached to the shaft for transmitting a torque from the graspable portion to the shaft portion.

In some cases the shaft portion has two such radially-expandable surfaces in hydraulic communication with the fluid reservoir and spaced apart from each other.

In some embodiments, the device has a second manually manipulable fluid reservoir defined within the graspable portion and in hydraulic communication with a second radially-expandable exterior surface.

In some embodiments, the radially-expandable surface of the shaft portion is constructed to return to a geometrically defined state from a radially-expanded state upon release of the graspable portion. By geometrically defined, I mean predefined and definite, such that the radially-expandable surface returns to essentially the same position on multiple cycles and in various situations.

The shaft portion may have a semi-rigid core including a first portion contiguously molded with the radially-expandable surface, and a second portion adjacent the first portion and of a similar diameter thereto.

In some configurations, the graspable portion is disposed generally on one side of a longitudinal axis of the shaft portion.

Another aspect of the invention features a method of providing sexual pleasure including inserting a phallus-shaped device with a defined initial shape into a body cavity capable of receiving sexual pleasure, such as a vagina or anus, squeezing a fluid-filled chamber rigidly attached to an end of the inserted device external to the body cavity to resiliently alter the shape of the device, and removing the device from the body cavity.

In some cases, squeezing the chamber radially expands a portion of the device within the body cavity.

In some configurations the radially expanding portion of the device, upon squeezing of the chamber, undergoes a continuously variable radial expansion.

The method may also include, with the device disposed within the body cavity, releasing the squeezed chamber to cause the device to return to its initial state.

In some instances the steps of inserting, squeezing and removing are all performed with one hand while maintaining a constant grip orientation on the chamber.

In some constructions the radially expanding portion of the device, upon squeezing of the chamber, alters in shape to form one or more discrete features.

In a system, the hand motions of self-pleasure of a first person are employed to automatically (or near-automatically) modulate an electronically actuated pleasure means to influence the self-pleasure of a second person through a data or audio communication means. Variously, the second person may be completely receptive. In either case the object is for second person may be optimally pleasured “transparently” to the intent of the first person. Electronically actuated pleasure means includes a vibratory device, a thrusting device, a device with rotating beads, a Sybian, or any other such pleasure device. In the preferred embodiment, a transfer function is used to optimize the experience for the second (receptive) person, even if the second person has a different natural pleasure rhythm than the first. Various means may be used to collect hand motion data from the first person. Also in the preferred embodiment, a cuff is used with a plurality of sensors built in to measure muscular contraction at various locations of the forearm, as known in the art. This may be used alone or in conjunction with an accelerometer(s) to provide overall motion displacement, the relative motions of different fingers, direction of motion (to or from the body) as well as timing and amplitude information concerning the relative motions at different portions of the hand. An accelerometer may be located on a finger, preferably held to the finger by a band that does not extend to the palm-side of the hand. The band therefore holds the finger grippingly from the sides. In another embodiment, a camera is used to collect raw visual data of hand motion. Regardless of the specific method used to collect hand motion data, this is provided to a microprocessor where it is reduced to specific classes of hand motions that need only be known internal to the system. These classes correlate with the variations associated with self-pleasuring such as displacement, velocity, acceleration and location of the hand, as well as degree of force being applied. If desired, this information is also available to individual fingers of the hand, as each portion of the wrist, both contractile and extensile may be measured. This data is transmitted by an audio or data channel such as telephone or computer data line to electronics that control a companion device attached to a second person such that hand motions from the first person contemporaneously affect operation of the companion device.

In a preferred embodiment the data is then manipulated by a transfer function that correlates the classes of hand motions with the classes of corresponding output motions of the companion (remote) device. Motion classes may be discrete, discrete ranges appended to one another to form a continuum of input and output response, or continuously variable. Another function of the transfer condition is to correlate the hand motions of the first person with pleasuring patterns specific to the second (receptive) person. This functionality allows two individuals with disparate pleasuring patterns to achieve sexual parity to a higher degree than they could without the transfer function, potentially a higher degree than they could if they were co-located. As one example, a first person who initiates high amplitude, low frequency motions early in the process and then low amplitude, high frequency motion near the end could (using the instant invention) cause the opposite effect in the pleasuring process of the second person (who prefers low amplitude, high frequency motions early in the process and high amplitude, low frequency motion at the end) by selection of the appropriate transfer function. Various aspects of the invention may therefore provide means for a first person to self-pleasure in such a way as to simultaneously create a pleasure stimulus in a remotely located second person such that the remotely located person is pleasured in a way that is both optimal and transparent to the first person. This can include the second person self-pleasuring with a device that includes mechanical actuation controlled by the motions of self-pleasure of the first person such that the stimulation received by the second person is a combined effort of their own actions and those the remotely located first person. Furthermore, in this class of device the system can operate in both directions simultaneously, so that each partner experiences there own self-pleasure with additional independent motions superimposed as a consequence of the output from the self-pleasure of the partner. A simple example would be two handheld vibratory devices. The large-scale motion of the device would be self-controlled. The amplitude and frequency of vibration (for both partners) would be passively controlled by the large-scale motions of the remotely located partner. In one embodiment the system includes an auxiliary input to indicate eminent climax; the system response by modifying the transfer function to alter the slope of the existing response, or to initiate a non-linear response. Additional input mat be provided by a dial that may manually indicate a short term personal preference or a switch to indicate eminent climax.

In the preferred embodiment, the transfer function is generated by the second person while the invention is in a manual or "learn" mode At any time during the "learning" process, the second person may modify the output and thereby the transfer function. The system learns what the second (receptive) partner prefers as a function of the experience they chose for them self, as based on the measured hand motions, device, and the amount of time the second person chooses to spend with each operational mode during each phase relative to the phase of the process. Another aspect of the invention is the incorporation of autonomic physiologic data into the transfer functions to vary the output(s) as a function of the physiologic state of one or both partners, data such as respiration rate, pulse rate, EKG, skin conductance, and skin temperature. This data may be measured utilizing various means known in the art.

The system may therefore build a customized mapping of "input to optimal output" (a sex-device transfer function) as a function of the input class, the phase of the process (as a function of time or measured physiologic response of one or both partners), and the output previously selected by the receptive person under similar sets of conditions. Superimposed on this transfer function a user may supply a manual input. Therefore, using these devices and methods, a given motion by a first person may result in a varying output response to be experienced by a remotely located second person, as a function of time in the process, the second person's personal preference, and/or physiologic response. Additionally, a manual control can influence the transfer function, especially to indicate the phase of the process, be it early, middle, or late.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 25*c* is also a cross-sectional view of the dildo of FIG. 23, taken along line 25*c*—25*c*.

FIG. 31 shows a schematic of a system that provides an optimized pleasuring experience to a second person (at a remote location) using the self-pleasuring motions of a first person as the instigating signal.

FIG. 32 shows the device of FIG. 29 with the addition of physiologic sensors, which can be collected automatically or manually.

Like reference symbols in the various drawings indicate like elements.

DETAILED DESCRIPTION

Figure 1:
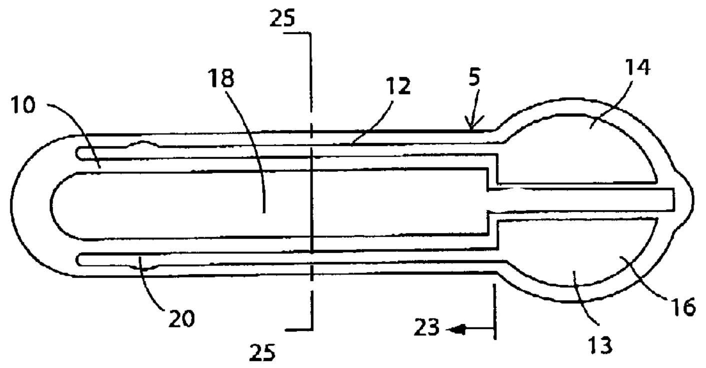
FIG. 1 shows a variable radius (size and shape) dildo with an extra ridge around the circumference in a relaxed state.

FIG. 1 shows a variable radius (size and shape) dildo 5 in its relaxed state. Elastomeric body 10 includes channels 12 in the shaft 23 connected to reservoir 14 at the base end 16. It is critical to operability of the device to provide structural integrity from the base end 16 to the distal end so that the device may be used to selectively apply force both parallel with and especially orthogonal to the primary axis while the device is in the body. To accomplish this goal, the reservoir 14 must be rigidly attached; specifically it must be attached with sufficient rigidity that it may be used (in effect) as a handle to manipulate the device. This includes the need to oppose the longitudinal and especially lateral forces common to such activity. “Longitudinal” is defined as being along the primary axis of the shaft and “lateral” is defined as orthogonal to the shaft’s primary axis. Furthermore, the shaft 23 of the device must be sufficiently rigid to transmit the lateral and longitudinal forces from the reservoir 14 to the distal end of the device, for the same reasons. Another way to express this is that the connection between the reservoir 14 and the proximal end of the shaft 23 should be attached with sufficiently rigidity that a useful and appropriate amount torque (i.e. approximately the same as any like device) may be transmitted from the hand grasping the reservoir 14 to the proximal end of the shaft 23. In turn, the shaft 23 should be sufficiently rigid that a torque placed upon its proximal end may be transmitted through to the distal end. An internal structural member 18 may be used to provide additional rigidity and may be made of a higher durometer material. The diameter of reservoir 14 should be greater than shaft 23 to provide an ample volume of fluid to expand channels 12 while maintaining a diameter suitable for continued use as a handle, including being of sufficient diameter to oppose the fore mentioned torque. Indent 20 is a variation in the thickness of the elastomeric material between the channels 12 and the surface of the device, in this case to form a ridge that extends around the circumference. Many variations of bumps and ridges are possible utilizing this approach, including multi-tiered features, that is additional features that appear as the reservoir 14 is squeezed more forcefully. Fluid 13 (such as air, water or oil) fills channels 12 and reservoir 14 such that it may be displaced back and forth between the two as a function of applied external force 66. That is to say when the external force 66 is removed, the device returns automatically to its neutral or relaxed state. The flow of fluid 13 causes a profound change to the shape of the device; thereby providing increased stimulation due to an overall displacement of fluid, not a velocity change. The device expands from a clearly defined base state, and for all intensive purposed cannot be compressed from that base state. The device is sealed at all times. The device may be said to have a single and clearly-defined lowest energy state (to which it returns whenever external forces 66 is removed) and a second (continuously variable) expansion state. The extent of the expansion in each region is controlled by varying the thickness of the cross sectional area or by modifying the durometer of the material. Valves may be incorporated a the extreme distal end to maintain a desired dimension. The location of the reservoir 14 at the end of (and integral with) the variable radius dildo 5 allows the user to perform a variety of actions with one hand, namely inward, outward, and radial motion of variable radius dildo 5 as well as actuation of the expansion state while still utilizing the reservoir 14 as a handle to transmit forces to the distal end of the device.

Figure 2:
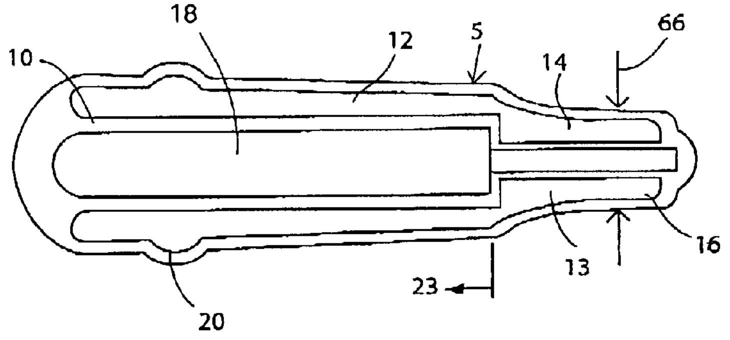
FIG. 2 shows the variable radius dildo of FIG. 1 in an expanded state.

FIG. 2 shows a variable radius dildo 5 in its expanded state. The base end 16 has been squeezed, forcing fluid from reservoir 14 into channels 12, causing them to enlarge and thereby increase the local radius of the dildo. The reduced material thickness at indent 20 causes a change in shape, specifically the ridge shown.

Figure 3:
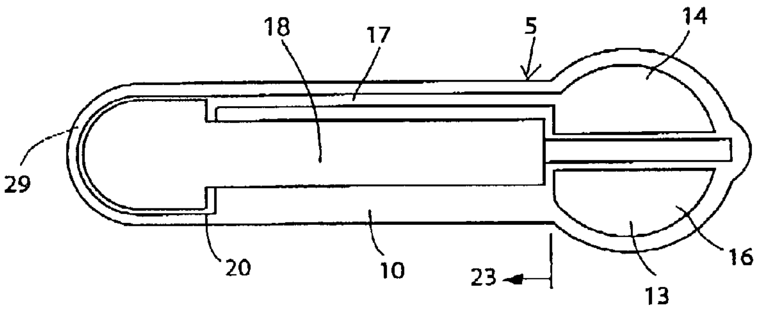
FIG. 3 shows a variable radius dildo with a bulbous head in a relaxed state.

FIG. 3 shows a variable dildo 5 with a bulbous head 29 in a relaxed state. The size variability is not over the entire length of the shaft 23, but limited to one region, in this case the distal end. Internal structural member 18 has an augmented end to support the interior of bulbous head 29. The internal structural member 18 provides a backing so that the outer membrane (web 54) has a defined limit to its inward displacement. For devices such as this (i.e. with regions of expandability and regions of non-expandability) this provides uniformity to the “feel” (compliance) between the two regions. For devices that have regions of the entire surface expandable, internal structural member 18 adds significant rigidity, thereby greatly enhancing the ability for the device to transmit lateral forces, yet still provide the function of a dynamically variable radius.)

Figure 4:
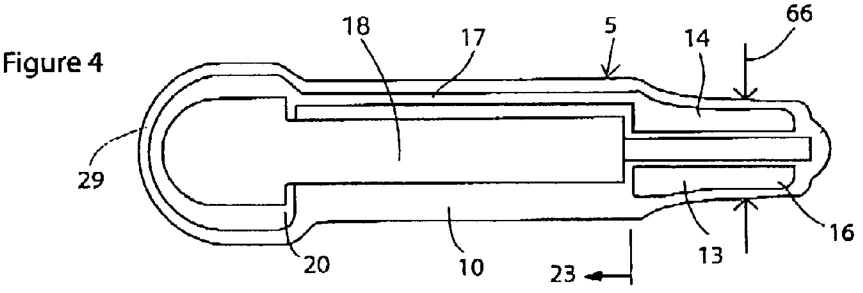
FIG. 4 shows the variable radius dildo of FIG. 3 in an expanded state.

FIG. 4 shows bulbous head 29 in an expanded state. Reservoir 14 is connected to bulbous head 29 through a non-expansive conduction channel 17.

Figure 5:
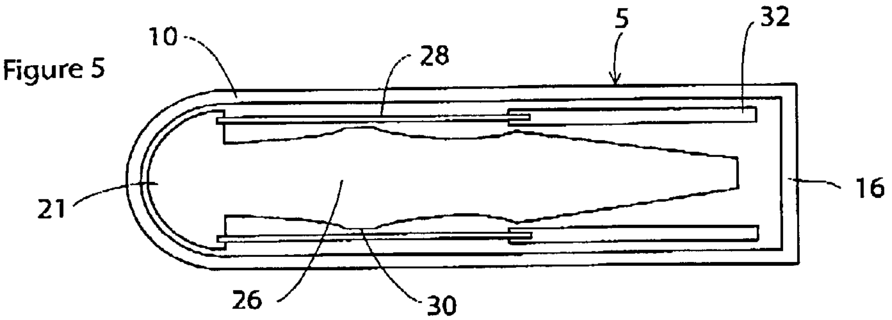
FIG. 5 shows a variable radius dildo with mechanical actuation means in a relaxed state.

FIG. 5 shows a variable radius dildo 5 with mechanical actuation means in its relaxed state. Elastomeric body 10 contains the mechanism inside. In the embodiment shown, a rigid plastic core 26 is centrally located. A plurality of flexible beams 28 are attached to the core on an insertion end 21, supported by a support area 30 and then attached to rigid levers 32 at base end 16.

Figure 6:
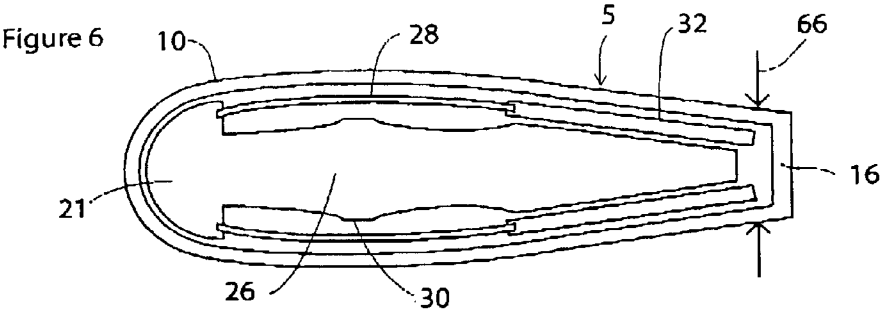
FIG. 6 shows the variable radius dildo of FIG. 5 in an expanded state.

FIG. 6 shows a variable radius dildo 5 with mechanical actuation means in its expanded state. By squeezing rigid levers 32 a force is placed on flexible beams 28, causing them to bulge outwards, and thereby vary the radius of the device.

Figure 7:
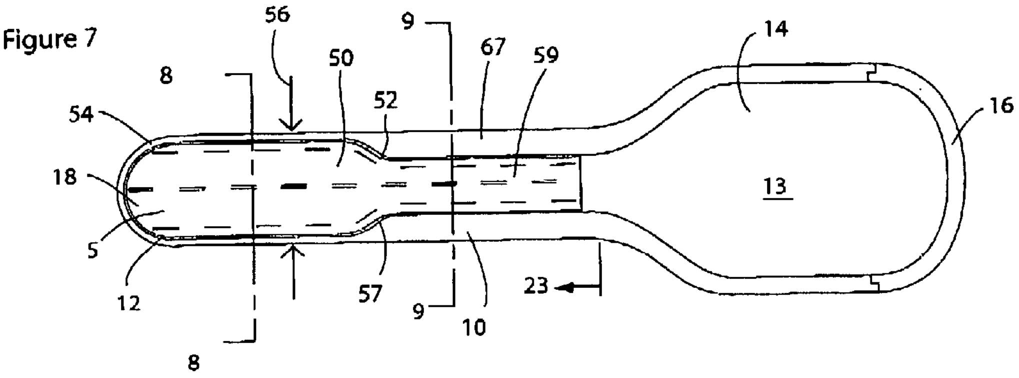
FIG. 7 shows a variable radius dildo with a separate core.

FIG. 7 shows a dynamically variable dildo 5 with a separate core 50, in a relaxed state. The size variability is not over the entire length of the shaft 23, but limited to one region, in this case the distal end. Without external force 66, the shaft 23 assumes its lowest energy shape. Separate core 50 was molded independently, inserted into elastomeric body 10 and not attached to base end 16. The neck 59 is grippingly engaged at thickened neck region 67. The elastomeric body 10 includes web 54, which closely conforms to separate core 50, creating channels 12 of essentially zero width. The benefit of zero-width channels 12 is that the user cannot detect a difference in compliance between the expandable and non-expandable regions of the device because the web 54 rests on the surface of separate core 50, a feature also shown in FIG. 3. Elastomeric body 10 includes a longitudinal restraint feature 57, here shown as the distal edge of thickened neck region 67. Longitudinal restraint feature 57 prevents separate core 50 from entering reservoir 14. The inner diameter of the thickened neck region 67 is less than the outer diameter of the neck 59, thus providing an interference fit that firmly secures the separate core 50 against lateral motion, creating the effect that the separate core 50 is integral to the elastomeric body 10 without any bonding material required. Not requiring a chemical bond at this location allows a significantly wider range of materials to be used, including dissimilar materials which would not bond together well. A secure fit of separate core 50 provides rigidity from the reservoir 14 (where the device is held) to the distal end, thereby allowing the user to apply lateral forces at the distal end, an important feature of a device of this application. Reservoir 14 is preferably of a larger relaxed diameter than the shaft 23, (in the relaxed state) thereby providing sufficient displacement for the expansion of web 54 and to do so while the reservoir 14 is sufficiently large to act as a handle capable of transmitting a useful torque placed upon it. Fluid 13 passes through the thickened neck region 67 and enters channel 12 through canals 52, which are preferably molded into separate core 50. Elastomeric body 10 is made of a highly compliant energy-storing material. For cast products the material should preferably bond to itself, such as a tin-based silicone with a durometer of 30 on the shore A scale.

Figure 8:
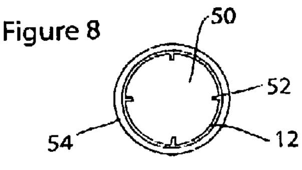
FIG. 8 shows a cross-sectional view, taken along line 8—8 in FIG. 7.

FIG. 8 shows a cross section through the expansive region of FIG. 7. Web 54 closely conforms to separate core 50. Separate core 50 supports web 54 by physical contact, rendering channels 12 as essentially zero-width. Preferably there is a slight interference in the dimensions between the web 54 and the separate core 50 so that web 54 fits snugly. Canals 52 are molded into separate core 50 providing entry of fluid 13 into the distal end of the expansive region.

Figure 9:
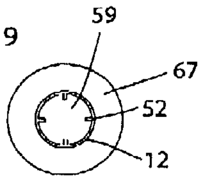
FIG. 9 shows a cross-sectional view, taken along line 9—9 in either FIG. 7 or FIG. 10.

FIG. 9 shows a cross section through the non-expansive region of FIG. 7. Fluid 13 may flow through canals 52, allowing thickened neck region 67 to conform tightly to neck 59. The narrowness of the canals 53 prevents ingress of the web 54, an undesirable surface feature. This region of shaft 23 does not change.

Figure 10:
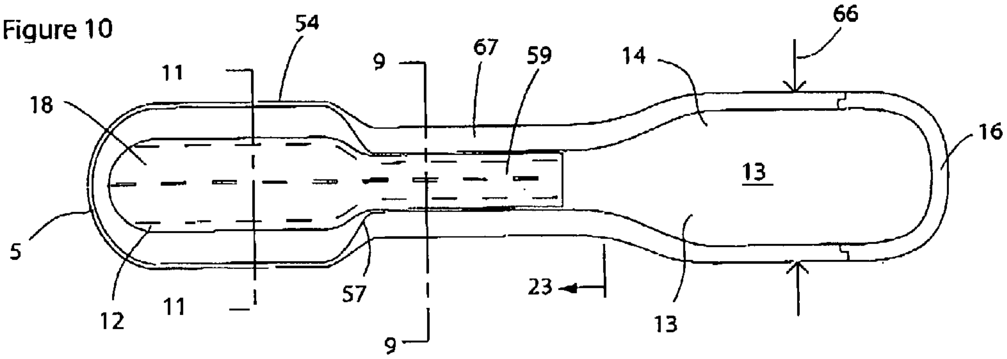
FIG. 10 shows the dildo of FIG. 5, in an expanded state.

FIG. 10 shows a dynamically variable dildo 5 with a separate core 50, in an expanded state. An external force 66 has been applied to the reservoir 14 forcing fluid through canals 52 and into channels 12. This action stores energy in web 54, energy that will be released when the web forces the fluid back into the reservoir 14. The distal end has grown in size (a larger, but constant radius), the central region is unchanged (see FIG. 9), and the region between the two has a continuously varying radius. The result is a profoundly different overall shape between the energized (expanded) and non-energized (relaxed) states. Thickened neck region 67 is tightly constrained to the neck 59 of separate core 50, and provides lateral stability to separate core 50, independent of whether web 54 is in the expanded or relaxed state. The location of the primary reservoir at the end of and integral with the device allows the user to perform a plurality of actions with one hand, namely motion of the device (insertion and removal) actuation of the internal motions of the device (inflation and deflation) as well as rotation of the device. All of these motions may be affected in any order, at any time, and with one hand.

Figure 11:
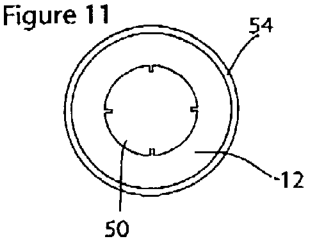
FIG. 11 shows a cross-sectional view, taken along line 11—11 in FIG. 10.

FIG. 11 shows a cross section through the expanded portion of FIG. 10. Web 54 is displaced from separate core 50 by fluid 13. Stresses in the web 54 act to automatically return dildo 5 to the relaxed state shown in FIGS. 7 and 8 as soon as the user ceases to apply external force 66. This section is expanded while the cross section through another section (FIG. 9) of shaft 23 is unchanged.

Figure 12:
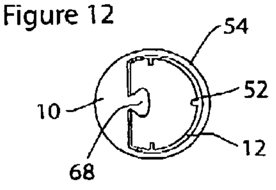
FIG. 12 shows a cross-sectional view through an asymmetrical expandable region of a dildo, in a relaxed state.

FIG. 12 shows a cross sectional view of an asymmetrical embodiment, in which the web 54 does not expand in all directions. Web 54 is supported from behind by a solid material, providing a consistent feel around the entire circumference of the cross section. The figure shows the device in a relaxed state.

Figure 13:
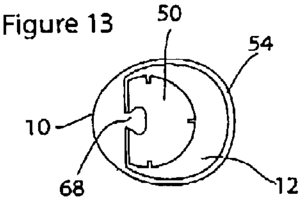
FIG. 13 shows the embodiment of FIG. 12 in an expanded state.

FIG. 13 shows the embodiment of FIG. 12 in an expanded state. With expansion localized to one side of the shaft 23, the device has a strong lateral asymmetry, providing the user distinctly different sensations as the device is rotated. This allows the user to selectively stimulate (or ignore) portions of the anatomy. Moreover, the user may use one hand to rotate the device to the desired orientation while selectively expanding or collapsing dildo 5, thereby contacting (or NOT contacting) specific regions, either intermittently, only once, or not at all. Interlocking feature 68 holds the non-expansive portion of elastomeric body 10 to separate core 50.

Figure 14:
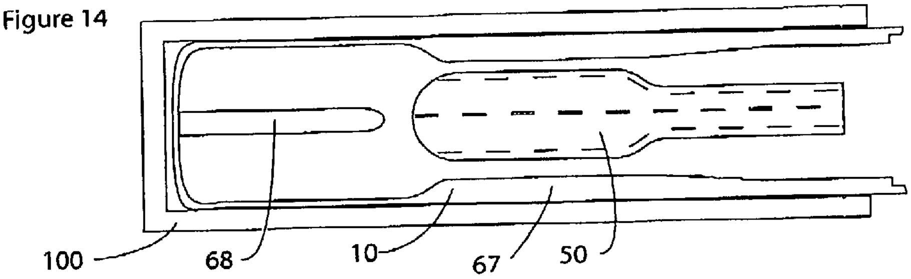
FIG. 14 shows an assembly method and apparatus, for forming dildos with separate cores.

FIG. 14 shows a method and apparatus to manufacture the embodiments shown with separate cores 50. Elastomeric body 10 is placed into vacuum chamber 100. The cap that forms base end 16 is as yet unattached. Applying a vacuum to the exterior of the elastomeric body 10 expands thickened neck region 67, allowing separate core 50 to be easily inserted and secured to interlocking feature 68.

Figure 15:
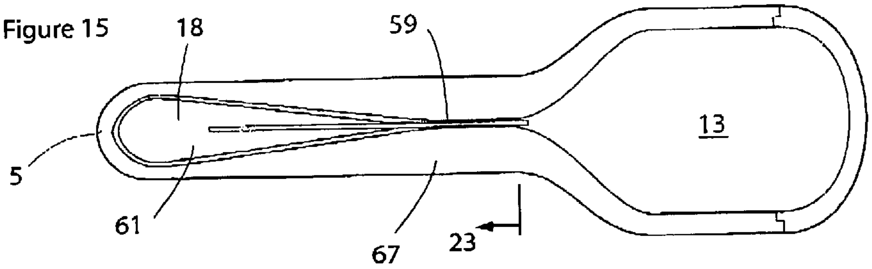
FIG. 15 shows a variation of FIG. 7 in which the separate core is predominantly conical.

FIG. 15 shows a variation of FIG. 7 in which the separate core 50 is predominantly conical. The neck 59 is provided by a rigid insert, made of engineering plastic or metal.

Figure 16:
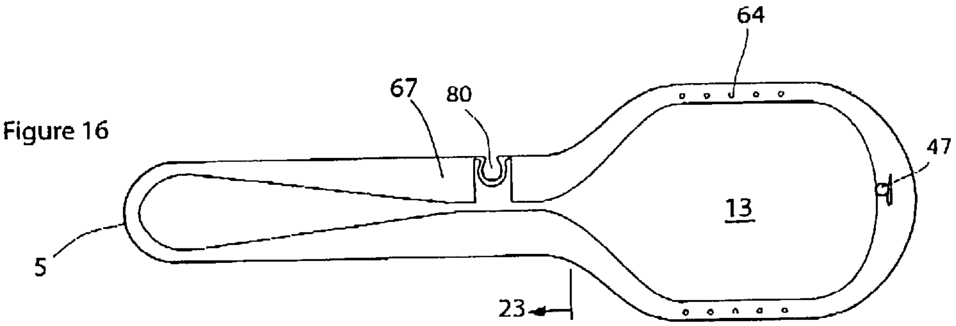
FIG. 16 shows an embodiment without a separate core.

FIG. 16 shows an embodiment in which the separate core 50 is omitted. Radial constraint feature 64 is made of fabric or a thin plastic web and prevents outward radial expansion when the shaft 23 is squeezed. The result is to simulate a solid core. This embodiment also shows the device manufactured by containing the fluid in a custom-shaped balloon prior to molding. This facilitates manufacturing the device in a single step. In other embodiments the balloon functionality is provided by a temporary rigid structure that degrades into the fluid over a relatively short period of time.

Figure 17:
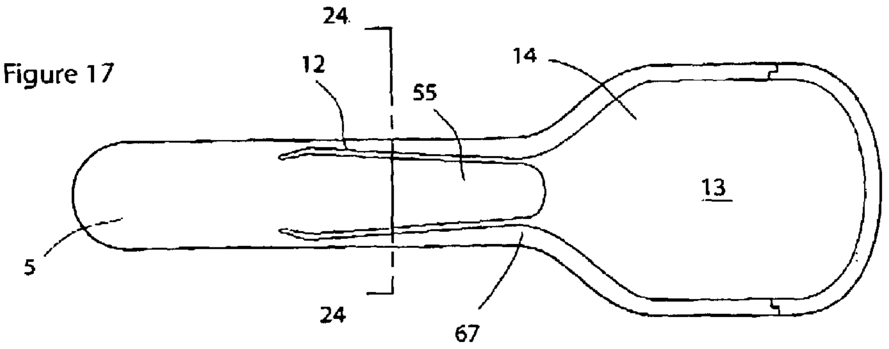
FIG. 17 shows a variable radius dildo with an integral core, in a relaxed state.

FIG. 17 shows a variable shape dildo 5 with an integral core 55 in a relaxed state. Whereas the embodiment of FIGS. 7 and 10 show expansion at the distal end, this embodiment shows expansion only in the proximal end of the shaft 23, as the location and type of expansion are a personal preference that differs from person to person. Here the wall thickness at the distal end is much thicker than in the expansive region, in fact, equal to the radius. Furthermore, the expansion varies even locally. To accomplish this end, web 54 is made with a variable (non-constant) thickness, providing different levels of expansion at different areas of the expansive region. In this example, the expansion is greater toward the distal end (of the expansive zone) than the proximal end. By modifying the thickness of the web 54, a wide variety of other profiles may be provided. The proximal end of integral core 55 is constrained laterally by thickened neck region 67. Because the reservoir 14 is rigidly and securely attached the phallus-shaped portion (shaft 23) of the device, the user may simultaneously: insert or withdraw; actuate the web 54 to any degree, within the range of the device; and rotate the device, all with a single hand. The degree of expansion of each channel 12, or sub-region within each channel, is controlled by the molded thickness of material on the exterior side of each region of the channel, and the type of material selected for that region. (Different durometers may be used along the external surface to further increase the designer's control over the design). Regions designed with thicker (or higher durometer) sections between the channel and the surface of the device will expand less while thin sections (or lower durometer) will expand more, providing a wide variety of embodiments including devices with regular undulations, randomized undulations, textures, and knobs. Although not shown, the surface may contain contour variations in the relaxed state.

The manufacturing technique varies from that of devices with separate cores. In this example the integral core 55 is molded as one piece with the web 54. The use of a flexible inner piece for the mold tooling and/or pressurized air may facilitate molding and/or removal of the elastomeric body 10 from the tool. The channels 12 may be circular or sectioned as shown in FIGS. 24*a–d* and 25*a–d*.

Figure 18:
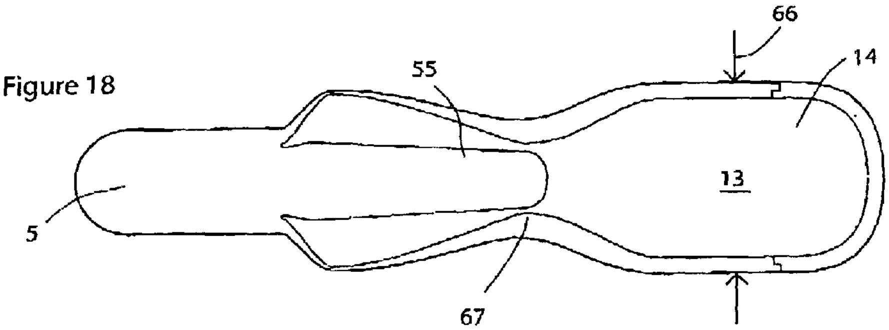
FIG. 18 shows the embodiment of FIG. 17 in an expanded state.

FIG. 18 shows the embodiment of FIG. 17 in an expanded state. Because thickened neck region 67 constrains integral core 55 from lateral motion, force may be conducted from reservoir 14 to the distal end of shaft 23.

Figure 19:
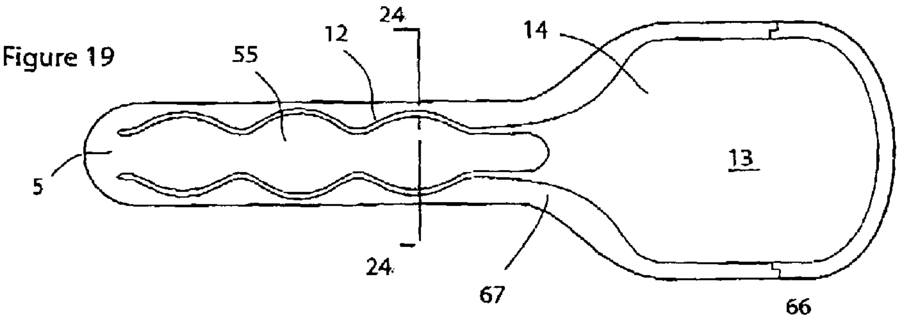
FIG. 19 shows an embodiment with an undulating variable surface pattern.

FIG. 19 shows a variation of the embodiment of FIG. 17 to create an undulating surface. The thickened regions will expand less. Two distinct levels of expansion are provided. The central ridge 78 will expands more than the other ridges 79.

Figure 20:
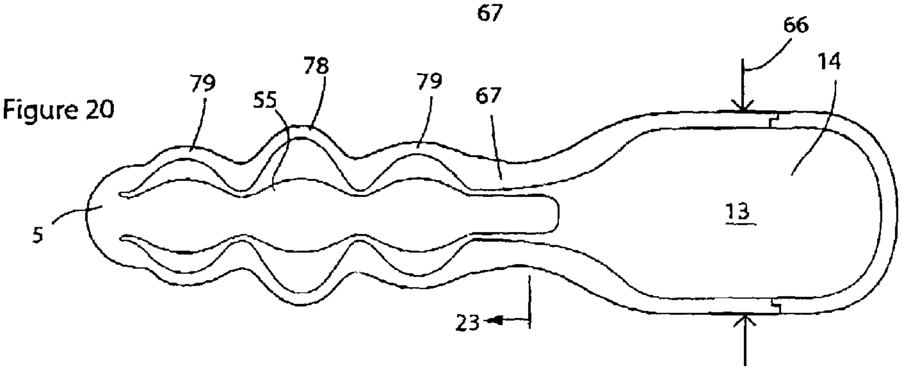
FIG. 20 shows the embodiment of FIG. 19 in an expanded state.

FIG. 20 shows the embodiment of FIG. 19 in an expanded state. The central ridge 78 has expanded more than other ridges 79. Because thickened neck region 67 constrains integral core 55 from lateral motion, force may be conducted from reservoir 14 to the distal tip of shaft 23.

Figure 21:
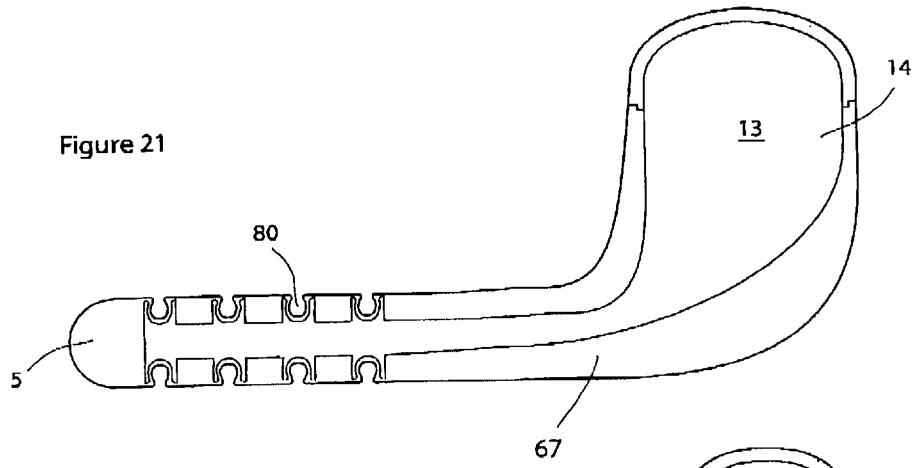
FIG. 21 shows a variable radius dildo with inwardly molded features in a relaxed state.

FIG. 21 shows a variable radius dildo 5 with inwardly molded features 80 in a relaxed state. The device is shown in its lowest energy state (to which it returns whenever external forces 66 are removed). Also shown is reservoir 14 rigidly attached off-axis such that reservoir 14 may be used as a handle to conduct force from throughout the device to the distal tip of shaft 23. The off-axis orientation provides improved accessibility to grasp dildo 5.

Figure 22:
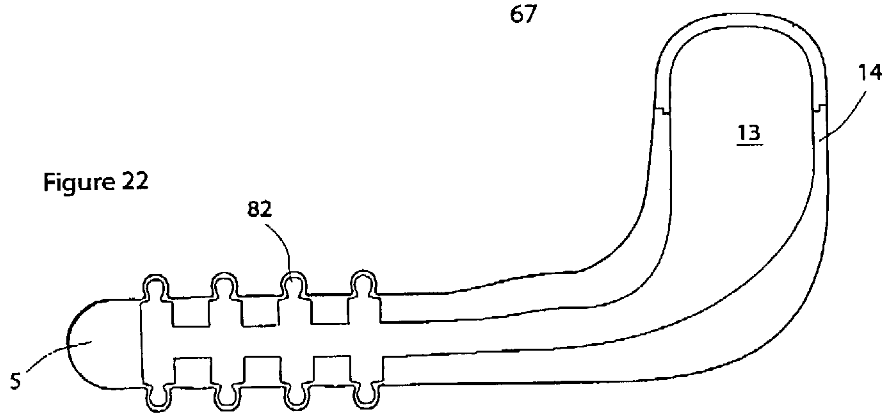
FIG. 22 shows the embodiment of FIG. 21 in an expanded state.

FIG. 22 shows a variable radius dildo 5 with inwardly molded features 80 in an expanded state. In this embodiment the energized (expanded) state is not variable, because the inwardly molded features 80 expand discontinuously (i.e. they pop into the position shown) as the internal pressure reaches a critical value.

Figure 23:
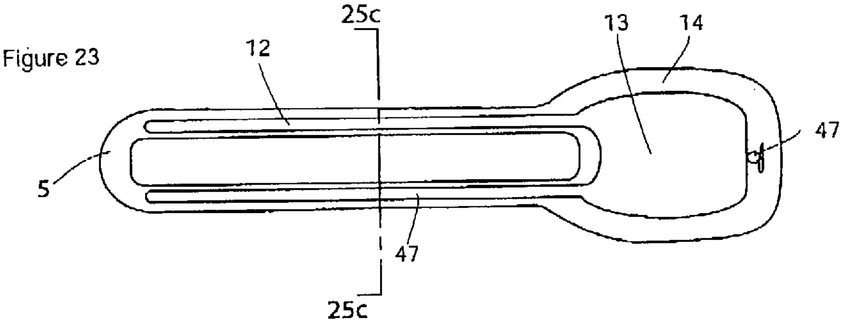
FIG. 23 shows a variable radius dildo in a relaxed state.

FIG. 23 shows a variable shape dildo 5 in a relaxed state. In this embodiment, the expansion is localized to two opposing sides along the length of the shaft, separated by regions of non-expansion, thereby closely mimicking the human anatomy. This embodiment also shows fluid 13 contained within balloon 47. The balloon 47 may be constrained during the manufacturing process by a light tack adhesive to an internal core 18, which may be in turn aligned with pins in the mold. This process has the advantages of containing the fluid 13 during the manufacturing process. Similarly a rigid version of the balloon shape may be used, especially if the material degrades over a relatively short period of time, leaving the elastomeric body 10 to contain the fluid 13.

Figure 24A:
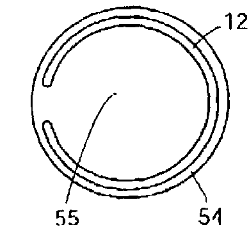
FIGS. 24*a*–24*d* are cross-sectional views of alternate constructions of the dildo of either FIG. 17 or FIG. 19, taken along line 24—24.

FIG. 24*a* shows a cross sectional view in which web 54 connected to an integral core 55 in one region along the circumference. Attachment in this way helps to orient web 54, especially to oppose frictional forces on the exterior surface of web 54 without displacing it.

Figure 24B:
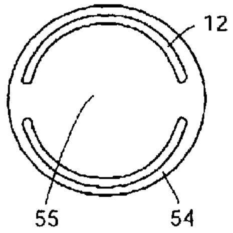

FIG. 24*b* shows web 54 connected to an integral core 55 in two regions along the circumference, increasing the ability of the device to orient web 54 over that of FIG. 24*a*.

Figure 24C:
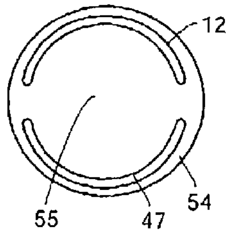

FIG. 24*c* shows a variant of FIG. 24*b* in which a balloon 47 is used to contain the fluid 13 prior to encasing in elastomeric body 10.

Figure 24D:
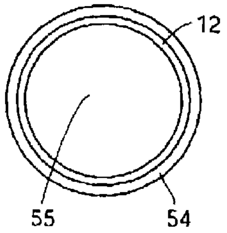

FIG. 24*d* shows a cross sectional view in which web 54 is not connected to an integral core 55.

Figure 25A:
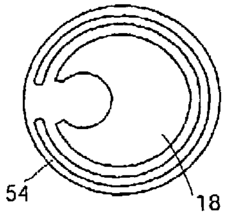
FIGS. 25*a*–25*d* are cross-sectional views of alternate constructions of the dildo of FIG. 1, taken along line 25—25.

FIG. 25*a* shows a cross sectional view in which web 54 is connected the rest of elastomeric body 10 in one region along the circumference, which is also molded to interlock with an internal structural member 18.

Figure 25B:
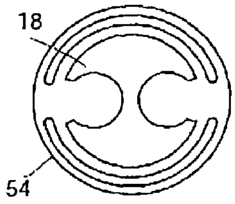

FIG. 25*b* shows web 54 connected the rest of elastomeric body 10 in two regions along the circumference, increasing the ability of the device to orient web 54 over that of FIG. 25*a*.

Figure 25C:
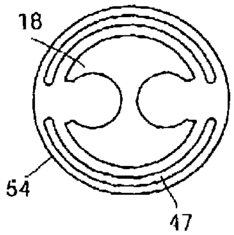

FIG. 25*c* shows a variant of FIG. 25*b* in which a balloon 47 is used to contain the fluid 13 prior to encasing in elastomeric body 10.

Figure 25D:
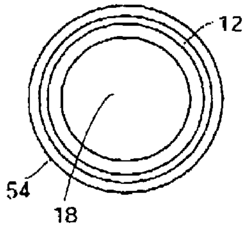

FIG. 25*d* shows a cross sectional view in which web 54 is not connected to internal structural member 18.

Figure 26:
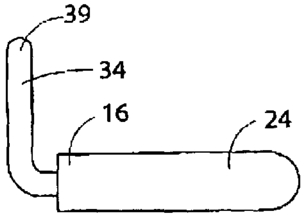
FIG. 26 shows a dildo with the base end attached to an extension.

FIG. 26 shows a dildo 24 with the base end 16 attached to an extension 34 at right angles to dildo 24. Extension 34 is rigid and acts as a handle providing a person improved accessibility to grasp dildo 24 when using the device on themselves. Extension 34 may be implemented as reservoir 14, as shown in FIGS. 21 and 22.

Figure 27:
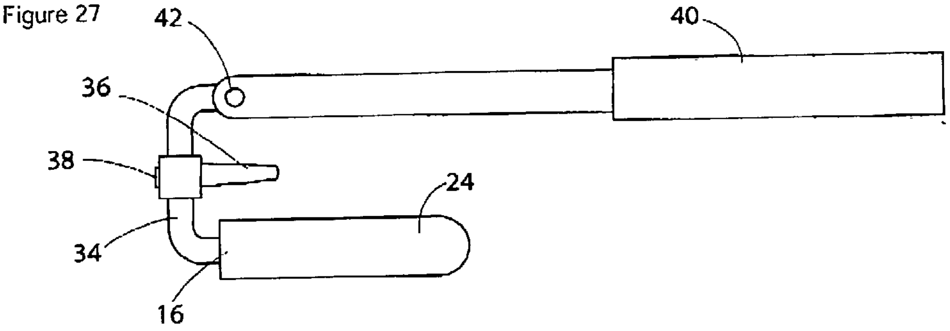
FIG. 27 shows a dildo with a protrusion attached to an extension.

FIG. 27 shows a dildo 24 with a protrusion 36 attached to extension 34. Protrusion 36 can extend into and out of the paper, forming a planar surface. Lock 38 allows protrusion 36 to be positioned at a variety of locations along extension 34. Handle 40 attaches to the exposed end 39 (shown in FIG. 3*a*) of extension 34. Handle 40 provides means for a user to manipulate dildo 24 while their hands remain in natural position on their chest or belly. This structure provides a tangible benefit of reducing the distance to contact the breasts and the intangible benefit of providing a psychological distance between the source of pleasure and the self provider of that pleasure, thereby increasing the user's perception of the involvement of a second party and improving the experience. Dildo 24 may also be detachable from extension 34 and/or handle 40, thereby providing for a plurality of devices to be there attached. Joint 42 provides means for a variable angle between the primary axes of handle 40 and dildo 24.

Figure 28:
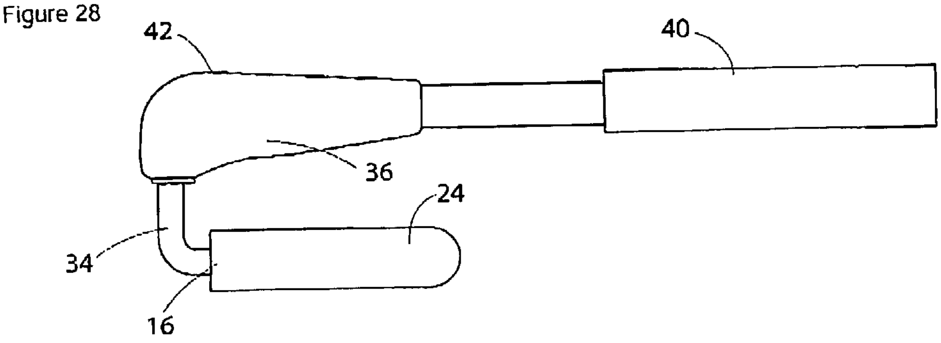
FIG. 28 shows protrusion molded into a handle and contoured to mimic the lower stomach region of a sexual partner.

FIG. 28 shows protrusion 36 molded into handle 40 and contoured to mimic the lower stomach region of a sexual partner. The devices of FIGS. 1 and 2 may be combined by manufacturing the reservoir 14 into the handle 40 and adding tubing that places reservoir 14 into fluidic contact with channels 12 through extension 34.

Figure 29:
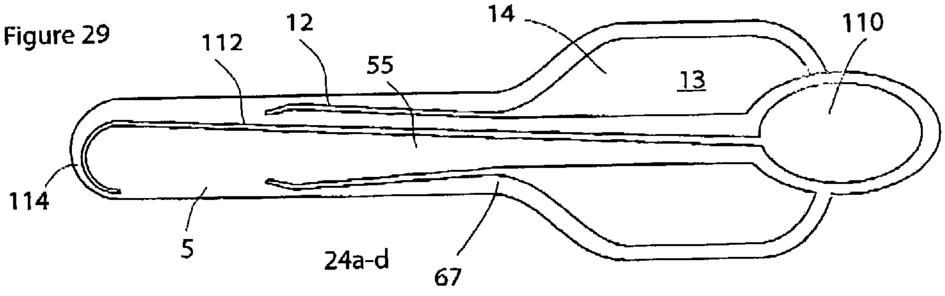
FIG. 29 shows a variable radius dildo with two independent fluidic chambers in a relaxed state.

Shape changing features may be independently actuated. FIG. 29 demonstrates this with a dildo including two independently variable shape-changing features, shown in a relaxed state. A secondary reservoir 110 is located next to reservoir 13. In this embodiment secondary reservoir 110 is located axially, but reservoirs 13 and 110 may be oriented differently to one another, such as laterally side-by-side, longitudinally end-to-end, or interspersed with half of each reservoir's volume located at the opposing diagonals of a clover-leaf pattern. The object is to provide the ability for the user to independently actuate two shape-changing features with one hand. Secondary reservoir 110 is connected by non-expansive conduction to an auxiliary expansion feature 114. By grasping the reservoirs 13 and 110 in different ways, a different set of shapes will appear and disappear as the hand is squeezed. In another use mode, the user may modify the manner in which they apply pressure to reservoirs 13 and 110, without needing to modify their grip to provide a different response from the device. For example, by squeezing with the fingers or squeezing with the fingers and the palm region.

Figure 30:
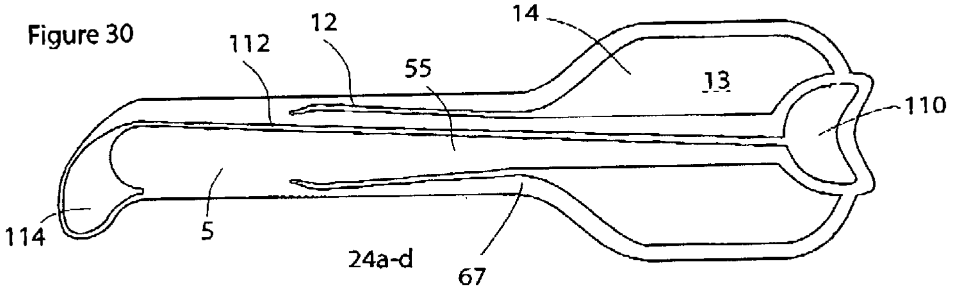
FIG. 30 shows a variable radius dildo with two independent fluidic chambers in an expanded state.

FIG. 30 shows the dildo of FIG. 29 with auxiliary expansion feature 114 in an expanded state. Secondary reservoir 110 has been squeezed, causing fluid to flow from it and through duct 112, thereby activating auxiliary expansion feature 114, shown here as an asymmetrically oriented finger-like protrusion near the distal end of the shaft 23. Many combinations are possible. Also while not shown, it is obvious that variable diameter dildos may be made to vibrate.

FIG. 31 shows a schematic of a system that provides an optimized pleasuring experience to a second person (at a remote location) using the self-pleasuring motions of a first person as the instigating signal. In the preferred embodiment, a plurality of strain sensors 46 measure contraction of muscles in the forearm. Sensors which detect electrical activity are also known. Accelerometer 48 provides additional information to a first central processing unit 50. First central processing unit 50 (and potentially a set of associated front-end electronics) converts the raw sensor data collected from strain sensors 46 and accelerometer 48 into a digital signal that may be reduced to a time-sequence of hand motions of the first person that fall into specified classes of motion, reflecting criteria such as: amplitude, force, frequency, and direction of motion. Other means, such as a video camera or sensors that measure location with electromagnetic fields may be used for the sensor of input device 44.

The classes of motion are then reduced to a series information packets 54 and transmitted via data or audio transmission means 56 to a remote location where a output correlation unit 58 is located. This transmission is performed using means known in the art, either through data lines or superimposed over the audio signal of a telephone call. The object is to transmit the collected data of the first person to the output correlation unit 58.

The output correlation unit 58 includes a central processing unit 60, an input module 64, signal conditioning electronics 62 and data storage 61. Conditioning electronics 62 includes D/A and the signal to power amplification (as known in the art) necessary to drive device 75. Data storage 61 contains data pertinent to the second person such as preferred settings, especially as they correlate with a variety of possible motion of a partner: a transfer function. Output correlation unit 58 accepts data from the first partner as well as input from the second partner for integration with the data in storage 61. Central processing unit 60 develops transfer functions for contemporaneous use to drive device 75 and for augmenting the data in storage 61. Input 64 can be used by the second partner to effect the operation of device 75 directly. This input is likewise used to modify the stored transfer function. Output from CPU 60 passes through signal conditioning electronics 62 to drive device 75 thereby providing the second party a sexual experience that is a function of the motions of the first party as well as their own personal preferences. Stimulation device 75 can be any electronic pleasure device designed to vary performance as a function of an external electrical signal, such as a vibratory device, a thrusting device, a device with rotating beads, an artificial orifice, or a Sybian. It is important to note that the system may be used reciprocally, meaning that both partners may have an input device 44 which is utilized in the control loop of an output correlation unit 58. Voice data may also be utilized, either for it's magnitude, or specific words may be detected with voice recognition.

This embodiment provides means for a couple to share a sexual experience remotely such that: neither person is focused on meeting the needs of the other thereby reducing their own pleasure; each partner enjoys an optimized experience, based on differing motions, even if their natural sexual motion patterns are different, thereby providing a sexual experience that may be more compatible than could be provided without the system; one or both partners may experience a self-pleasuring experience that not only has sensation beyond that of self-pleasure, but in ways that are integral with the motions of their partner.

FIG. 32 shows the device of FIG. 29 with the addition of physiologic sensors 111, which can be collected automatically or manually. This embodiment improves on the embodiment of FIG. 29 by compensating for timing differences that are sometimes inherent in the varying sexual characteristics of sexual partners at any given moment during the process, as well as providing means to better correlate the climax of remotely located individuals. Automatic physiologic data collection is done with autonomic physiologic input sensors 88 to measure parameters such as blood pressure, blood oximetry, skin conductivity and the like. Such sensing is known in the art. Physiologic data may also be collected manually with intensity inputs 113. Examples of intensity inputs 113 are dial input 100 with which the user can characterize perceived sexual intensity and climax button 101, which the user presses when climax is imminent. When the climax button 101 is pressed, the system provides an appropriate stimulus to the other partner to make the experience more contemporaneous for both. Physiologic sensors 111 on one or both partners may be utilized to modulate the transfer function (and hence the output signal used to drive device 75) as a function of time to provide an optimized experience for any receptive partner. Note that the system may be used reciprocally to enhance the experience for two or more partners simultaneously. Physiologic sensors 111 may be used to extend the length of the overall experience, and/or to coordinate the climax(es) of the partners. ID code data (transmitted in packet data 54) may also be included in the stored data so that predictive algorithms may be made to better correlate partners over repeated experiences. As in FIG. 33, the system can operate reciprocally.

Figure 33:
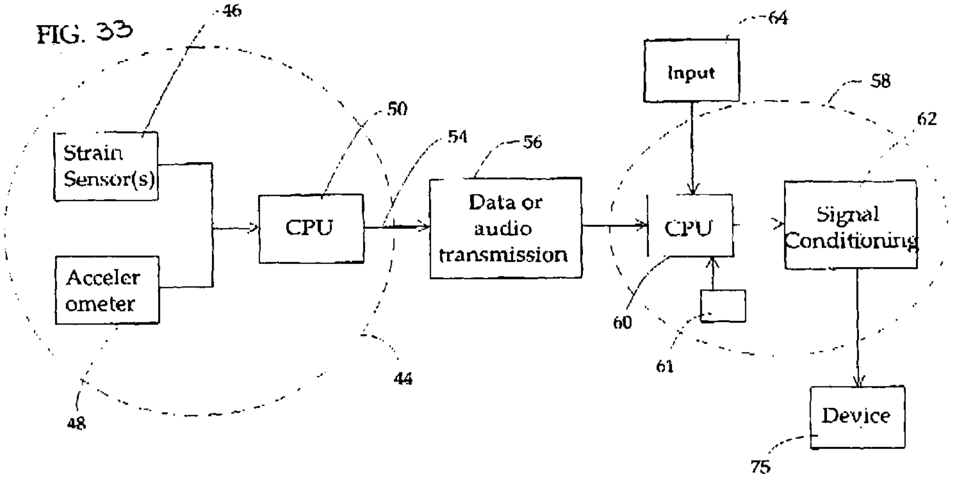
FIG. 33 shows an arm of a user with a cuff containing strain sensors and accelerometer.

FIG. 33 shows an arm 70 of a user with a cuff 72 containing strain sensors 46 and accelerometer 48. One cuff 72 may be used on each arm 70. An additional accelerometer 48 is shown on a finger, connected to cuff 72 by cable 77. Physiologic input 88 measures data such as pulse rate, blood pressure, EKG, blood oximetry, skin conductivity, skin temperature, and the like. Such sensing is known in the art. This data, as well as other physiologic sensors may be utilized by the system to monitor the stages of the sexual experience, and thereby to modulate the transfer function accordingly. Dial input 100 may be used to characterize perceived intensity or level of activity and a climax button 101 may be used to indicate eminent climax.

Figure 34:
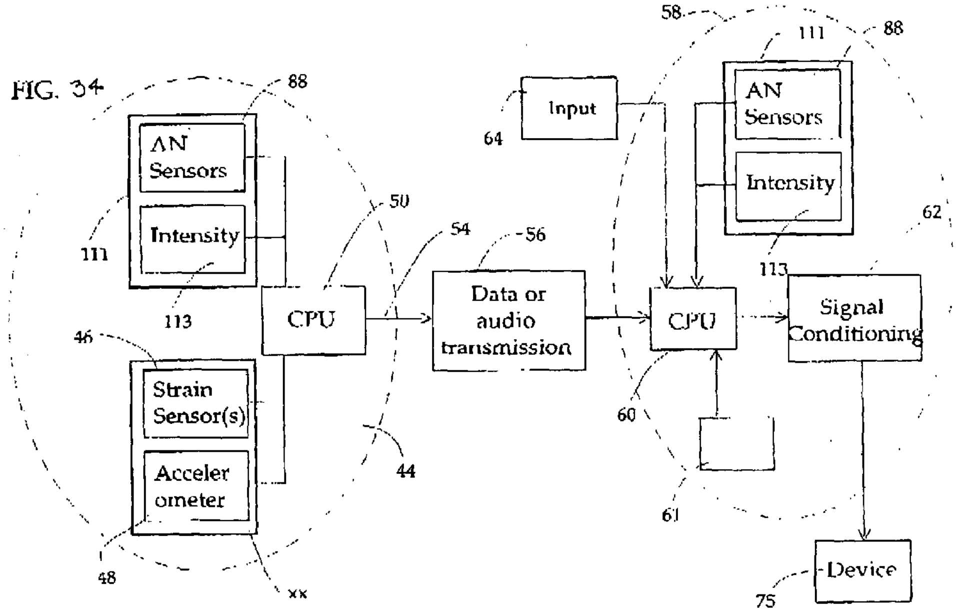
FIG. 34 shows a table with examples of transfer function correlations.

FIG. 34 shows a table with examples of transfer function correlations. Input data from sources on the left, may be controlled by the transfer function to result in the output responses on the right, in any combination. For example, a measured high force of short duration from the first user that occurs during a measured period of long duration of low frequency motion may result in a output response of high amplitude, low frequency motion in the device of the second user. Variously, stored control data may be used to augment or replace the input data from the second person. The central processing unit 60 may modulate modifications to the output signals given to device 75 by imposing a gradual shift one output response to the next.

While several embodiments have been described, it will be apparent to one skilled in the art how these embodiments may be varied (or combined with each other) and yet remain within the scope of the instant invention. The scope of the invention shall therefore be defined by the claims that follow.

What is claimed is:

1. A method of providing sexual pleasure, the method including grasping a phallus-shaped device with a first hand;

inserting the device with a defined initial shape into a body cavity capable of receiving sexual pleasure;

moving said device in a predominantly linear reciprocal motion; and, while grasping said device with said first hand, radially expanding a first portion of a shaft of said device with said first hand.

2. The method of claim 1 wherein radially expanding the first portion of the shaft changes an overall shape of the shaft.

3. The method of claim 2 further including returning said shaft to an original state by relaxing the grasp of said first hand.

4. The method of claim 2 wherein said change of shape is effected through fluid displacement.

5. The method of claim 2 wherein said shaft includes a second portion that maintains essentially a constant radius as the first portion is radially expanded.

6. The method of claim 5 wherein the shaft has a wall thickness in its second portion greater than a wall thickness in its first portion.

7. The method of claim 5 wherein the second portion of the shaft is radially solid.

8. The method of claim 7 wherein the first and second portions extend side- by-side along the shaft.

9. The method of claim 7 wherein the second portion forms a band about a circumference of the shaft.

10. The method of claim 1 wherein radially expanding the first portion of the shaft includes increasing a size of a localized feature at an outer surface of the shaft.

11. The method of claim 1 wherein said moving and said expanding occur simultaneously.

12. The method of claim 1 wherein said moving and expanding are performed while holding said device with said first hand in a single grip orientation.

13. The method of claim 1 wherein said first hand grasps a deformable portion of the phallus-shaped device containing a fluid reservoir.

14. The method of claim 13 wherein the deformable portion has a significantly larger diameter than said shaft.

15. The method of claim 13 further including transmitting a lateral force as applied by the hand grasping the reservoir to a distal end of the device through a relatively rigid connection therebetween.

16. The method of claim 1 wherein radially expanding a first portion of a shaft includes radially expanding two radially-expandable surfaces of the shaft, the two radially-expandable surfaces being in hydraulic communication with a fluid reservoir within the device, and spaced apart from each other.

17. The method of claim 1 wherein the shaft has a semi-rigid core including a first core portion contiguously molded with said radially expanded shaft portion, and a second core portion adjacent the first core portion and of a similar diameter thereto.

18. The method of claim 1 wherein the device defines a permanently sealed internal volume.

19. The method of claim 18 wherein radially expanding the first portion of the shaft changes an overall shape of the shaft.

20. The method of claim 19 further including returning said shaft to an original state by relaxing the grasp of said first hand.

21. The method of claim 19 wherein said change of shape is effected through fluid displacement.

22. The method of claim 19 wherein said shaft includes a second portion that maintains essentially a constant radius as the first portion is radially expanded.

23. The method of claim 22 wherein the shaft has a wall thickness in its second portion greater than a wall thickness in its first portion.

24. The method of claim 22 wherein the second portion of the shaft is radially solid.

25. The method of claim 24 wherein the first and second portions extend side-by-side along the shaft.

26. The method of claim 24 wherein the second portion forms a band about a circumference of the shaft.

27. The method of claim 18 wherein radially expanding the first portion of the shaft includes increasing a size of a localized feature at an outer surface of the shaft.

28. The method of claim 18 wherein said moving and said expanding occur simultaneously.

29. The method of claim 18 wherein said moving and expanding are performed while holding said device with said first hand in a single grip orientation.

30. The method of claim 18 wherein said first hand grasps a deformable portion of the phallus-shaped device containing a fluid reservoir.

31. The method of claim 30 wherein the deformable portion has a significantly larger diameter than said shaft.

32. The method of claim 30 further including transmitting a lateral force as applied by the hand grasping the reservoir to a distal end of the device through a relatively rigid connection therebetween.

33. The method of claim 18 wherein radially expanding a first portion of a shaft includes radially expanding two radially-expandable surfaces of the shaft, the two radially-expandable surfaces being in hydraulic communication with a fluid reservoir within the device, and spaced apart from each other.

34. The method of claim 18 wherein the shaft has a semi-rigid core including a first core portion contiguously molded with said radially expanded shaft portion, and a second core portion adjacent the first core portion and of a similar diameter thereto.

35. A method of providing sexual pleasure including:

inserting a phallus-shaped device with a defined initial shape into a body cavity capable of receiving sexual pleasure;

squeezing a fluid-filled chamber rigidly attached to an end of the inserted device external to said body cavity to resiliently alter the shape of the device;

removing the device from the body cavity; and reinserting the device with the device still in its altered shape.

36. The method of claim 35 wherein squeezing the chamber radially expands a portion of the device within the body cavity.

37. The method of claim 36 wherein, upon squeezing of the chamber, the radially expanding portion of the device undergoes a continuously variable radial expansion.

38. The method of claim 35 further including, with the device disposed within the body cavity, releasing the squeezed chamber to cause the device to return to its initial state.

39. The method of claim 38 wherein the steps of inserting, squeezing and removing are all performed with one hand while maintaining a constant grip orientation on the chamber.

40. The method of claim 35 wherein, upon squeezing of the chamber, the radially expanding portion of the device alters in shape to form one or more discrete features.

41. The method of claim 35 further including rotating the device.

42. The method of claim 35 wherein the squeezing step is performed before the inserting step.

43. The method of claim 35 wherein all steps are performed with one hand.

44. The method of claim 35 wherein the device and chamber together define a permanently sealed volume.

45. A device for sexual pleasure comprising:

a longitudinally rigid shaft portion for insertion into a human body, the shaft portion having a radially-expandable exterior surface in a discrete region thereof; and a graspable portion rigidly secured to one end of the shaft portion and containing a manually manipulable fluid reservoir in hydraulic communication with the radially-expandable surface for altering an outer shape of the shaft portion in response to manual manipulation of the graspable portion, the shaft and graspable portions together defining a permanently sealed volume;

wherein the radially-expandable surface is an exposed surface of an outer wall of the shaft portion that varies in thickness along the radially-expandable surface and has a contoured exterior surface when radially expanded, said contoured exterior surface defining undulations.

46. The device of claim 45 wherein the shaft portion also includes a non-deformable surface region.

47. The device of claim 46 wherein said non-deformable surface region is disposed near a proximal end of the shaft.

48. The device of claim 46 wherein said non-deformable surface region is disposed intermittently along a length of the shaft.

49. A device for sexual pleasure comprising:

a longitudinally rigid shaft portion for insertion into a human body, the shaft portion having a first radially-expandable exterior surface in a discrete region thereof, and a second radially-expandable exterior surface;

a graspable portion rigidly secured to one end of the shaft portion and containing a first manually manipulable fluid reservoir in hydraulic communication with the first radially-expandable surface for altering an outer shape of the shaft portion in response to manual manipulation of the graspable portion; and a second manually manipulable fluid reservoir defined within the graspable portion and in hydraulic communication with the second radially-expandable exterior surface.

50. The device of claim 49 wherein the graspable portion is attached to said shaft for transmitting a manually-induced motion from the graspable portion to the shaft portion.

51. The device of claim 49 wherein the graspable portion is of a greater diameter than the shaft portion.

52. The device of claim 49 wherein the shaft portion also includes a non-deformable surface region.

53. The device of claim 49 wherein the first radially-expandable surface is an exposed surface of an outer wall of the shaft portion that varies in thickness along the first radially-expandable surface.

54. The device of claim 49 wherein the graspable portion is attached to said shaft for transmitting a torque from the graspable portion to the shaft portion.

55. The device of claim 49 wherein the shaft portion has two radially-expandable surfaces in hydraulic communication with the first fluid reservoir and spaced apart from each other.

56. The device of claim 49 wherein the shaft portion has a semi-rigid core including a first portion contiguously molded with said first radially-expandable surface, and a second portion adjacent the first portion and of a similar diameter thereto.

57. The method of claim 49 wherein the shaft and graspable portions together define a permanently sealed volume.

58. A device for sexual pleasure comprising:

a longitudinally rigid shaft portion for insertion into a human body, the shaft portion having a radially-expandable exterior surface in a discrete region thereof; and a graspable portion rigidly secured to one end of the shaft portion and disposed generally on one side of a longitudinal axis of the shaft portion, the graspable portion containing a manually manipulable fluid reservoir in hydraulic communication with the radially-expandable surface for altering an outer shape of the shaft portion in response to manual manipulation of the graspable portion;

wherein the shaft and graspable portions together defining a permanently sealed volume.

59. The device of claim 58 wherein the graspable portion is attached to said shaft for transmitting a manually-induced motion from the graspable portion to the shaft portion.

60. The device of claim 58 wherein the graspable portion is of a greater diameter than the shaft portion.

61. The device of claim 58 wherein the shaft portion also includes a non-deformable surface region.

62. The device of claim 61 wherein said non-deformable surface region is disposed in an orientation from a list consisting of: linearly along a length of the shaft, near a distal end of the shaft, near a proximal end of the shaft, intermittently along a length of the shaft, and asymmetrically disposed upon one side of the shaft.

63. The device of claim 58 wherein the radially-expandable surface is an exposed surface of an outer wall of the shaft portion that varies in thickness along the radially-expandable surface.

64. The device of claim 58 wherein the graspable portion is attached to said shaft for transmitting a torque from the graspable portion to the shaft portion.

65. The device of claim 58 wherein the shaft portion has two such radially-expandable surfaces in hydraulic communication with the fluid reservoir and spaced apart from each other.

66. The device of claim 58 wherein the shaft portion has a semi-rigid core including a first portion contiguously molded with said radially-expandable surface, and a second portion adjacent the first portion and of a similar diameter thereto.

67. A device for sexual pleasure comprising:

a longitudinally rigid shaft portion for insertion into a human body, the shaft portion having a radially-expandable exterior surface in a discrete region thereof; and a graspable portion rigidly secured to one end of the shaft portion, disposed generally on one side of a longitudinal axis of the shaft portion, and containing a manually manipulable fluid reservoir in hydraulic communication with the radially-expandable surface for altering an outer shape of the shaft portion in response to manual manipulation of the graspable portion, the shaft and graspable portions together defining a permanently sealed volume;

wherein the radially-expandable surface has a contoured exterior surface when radially expanded, said contoured exterior surface defining undulations.

* * * * *